(12) United States Patent
Balschat et al.

(10) Patent No.: US 6,595,944 B2
(45) Date of Patent: Jul. 22, 2003

(54) DIALYSIS MACHINE AND METHOD OF OPERATING A DIALYSIS MACHINE

(75) Inventors: Klaus Balschat, Schwebheim (DE); Michael Koch, Schweinfurt (DE); Elmar Wolter, Estenfeld (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/882,337

(22) Filed: Jun. 15, 2001

(65) Prior Publication Data

US 2002/0088752 A1 Jul. 11, 2002

(30) Foreign Application Priority Data

Jun. 17, 2000 (DE) .......................... 100 29 892
Jul. 14, 2000 (DE) .......................... 100 34 368

(51) Int. Cl.[7] .................... A61M 37/00; C02F 61/00
(52) U.S. Cl. .................... 604/6.09; 604/6.11; 604/5.04; 210/646; 210/645
(58) Field of Search .................... 210/645–647, 210/321.71; 604/6.09, 6.11, 29, 30, 31, 4.01, 5.01, 5.04

(56) References Cited

U.S. PATENT DOCUMENTS

| 4,136,708 A | * | 1/1979 | Cosentino et al. | 137/99 |
|---|---|---|---|---|
| 4,702,829 A | * | 10/1987 | Polaschegg et al. | 210/195.2 |
| 4,770,769 A | * | 9/1988 | Schael | 210/104 |
| 5,522,998 A | * | 6/1996 | Polaschegg | 210/109 |
| 5,542,919 A | | 8/1996 | Simon et al. | |
| 6,042,784 A | * | 3/2000 | Wamsiedler et al. | 422/44 |
| 6,325,774 B1 | * | 12/2001 | Bene et al. | 210/321.71 |

FOREIGN PATENT DOCUMENTS

| DE | 28 38 414 | 3/1980 |
|---|---|---|
| DE | 30 06 718 | 9/1981 |
| DE | 197 08 391 | 10/1998 |
| DE | 199 29 327 | 12/2000 |

* cited by examiner

*Primary Examiner*—Angela D. Sykes
*Assistant Examiner*—Leslie R Deak
(74) *Attorney, Agent, or Firm*—Kenyon & Kenyon

(57) ABSTRACT

A machine and method for preparing dialysis fluid for a dialysis machine. Fresh water is mixed with one or more dialysis fluid concentrates. The mixture of water and concentrates is conveyed into an equalizing chamber by a proportioning unit at a predetermined flow rate independent of the dialysate flow rate. Metered addition of the concentrates is performed volumetrically and is monitored on the basis of the conductivity of the dialysis fluid, which is measured by conductivity sensors. Because the mixture of water and concentrates is always conveyed at the same flow rate, the composition of the dialysis fluid can be determined with a high accuracy and the proportioning can be performed accurately.

20 Claims, 3 Drawing Sheets

DIALYSIS MACHINE AND METHOD OF OPERATING A DIALYSIS MACHINE

TECHNICAL FIELD OF THE INVENTION

The present invention relates to a dialysis machine having a proportioning device for supplying dialysis fluid for a dialysis treatment and a method of operating a dialysis machine.

BACKGROUND OF THE INVENTION

To prepare dialysis fluid today it is customary in most cases to use prefabricated dialysis concentrates that need only be diluted with an appropriate amount of water. To avoid removing heat from blood during dialysis, the dialysis fluid is heated to body temperature. Furthermore, air dissolved in the dialysis fluid is removed by degassing.

The operation of mixing water and concentrate in a certain quantity ratio is referred to in general as proportioning. There are known proportioning devices where the metering is based not on a predetermined volume ratio but instead on reaching a certain electric conductivity in the resulting mixture. For conveying water and concentrate, proportioning devices that operate according to conductivity have pumps whose flow rates are regulated as a function of the measured conductivity to yield a dialysis fluid having the desired composition.

Because of the large exchange volumes, there is a need for accurate balancing of the fluid removed and the fluid supplied over the entire treatment period with the known dialysis machines. Volumetric balancing machines are state of the art.

German Patent Application 28 38 414 A discloses a dialysis machine having a volumetric balancing system. The balancing system is made of two chambers subdivided by a movable partition, each having an inlet line for fresh dialysis fluid and an outlet line for spent dialysis fluid. Cutoff valves controlled by a control unit are arranged in the inlet and outlet lines. The balancing system is operated in such a way that fresh dialysis fluid is alternately supplied to the two balancing chambers from one dialysis fluid source and spent dialysis fluid is removed at the same time.

To prepare the dialysis fluid with the known dialysis machines, water is generally mixed with one or more concentrates in a reservoir. The addition of concentrate takes place in accordance with the cycle of the balancing chamber of the balancing system, while the addition of water is regulated by a liquid level sensor in a reservoir that controls the water inlet valve as a function of the liquid level in the reservoir. If there is a change in flow rate, the proportioning becomes less accurate. Changes in flow rate occur, for example, in filling programs when a great deal of gas is produced in degassing the fluid coming from the dialyzer, or when there is a change in the hydraulic resistance in the tubing lines. These factors cause a change in the cycling of the concentrate pumps, but the water supply remains almost unaffected by this. These factors can lead to a change in the water-concentrate mixing ratio. In addition, these changes in pressure and flow have an effect on the injection points of the concentrates, which can also lead to problems in proportioning.

German Patent 30 06 718 describes a dialysis machine in which the proportioning of the dialysis fluid is accomplished by the balancing chamber of the balancing system. Therefore, concentrate is added when filling the chamber with fresh water.

SUMMARY OF THE INVENTION

The object of the present invention is to create a dialysis machine having a proportioning device for supplying dialysis fluid that will allow proportioning with a high accuracy regardless of flow rates. Another object of the present invention is to provide a method with which dialysis fluid can be proportioned for a dialysis machine with a high accuracy.

In one embodiment of the invention a dialysis machine is provided that includes a dialyzer subdivided by a semipermeable membrane into a chamber for a liquid to be purified and a dialysis fluid chamber. A dialysis fluid inlet line lead to an inlet of the dialysis fluid chamber. A dialysis fluid outlet line leads away from an outlet of the dialysis fluid chamber. A balancing system is also provided and is connected to the dialysis fluid inlet and outlet lines for balancing fresh and spent dialysis fluid. Also included is a proportioning device for supplying fresh dialysis fluid. The proportioning device includes a water source and at least one proportioning unit. The proportioning unit has a first chamber half and second chamber half configured to operate so that liquid is displaced from one chamber half when the other chamber half is filled with liquid. An inlet line leads from the water source and connects to an inlet of the first chamber half and an inlet the second chamber half. An outlet line connects to an outlet of the first chamber half and an outlet of the second chamber half. This allows the chamber halves to be alternately filled and emptied. At least one mixing point is provided in the inlet line or the outlet line. At least one dialysis fluid concentrate source supplies a fluid concentrate to a mixing point for forming a fresh dialysis fluid. An equalizing chamber is provided for the fresh dialysis fluid. The equalizing chamber is connected to the outlet line.

This invention makes it possible to separate the addition of concentrate from the balancing of dialysis fluid added and removed. The proportioning device can be installed in the known dialysis machines without any great changes in the equipment design. However, it may also form an independent unit, which is connected to a dialysis machine.

The advantages of this invention include the fact that a concentrate or more than one concentrate is/are always added at a certain flow rate regardless of which dialysis fluid flow rate is set. Since the concentrates and water are always mixed at a certain flow rate, the concentrate and water can be proportioned accurately to achieve a certain conductivity.

The flow rate is set by alternately filling the first and second chamber halves of a proportioning device, such that when filling one half of the chamber, liquid is displaced from the other half of the chamber. The flow rate is based on the volume of the chamber halves and the filling time and emptying time, which can be set with precision by switching cutoff elements arranged in the inlet and outlet lines of the chamber halves.

The proportioning device may include just one proportioning chamber which is subdivided by a movable partition into two chamber halves. However, each chamber half may also be part of its own separate proportioning chamber, each having a separate displacement element coupled together so that liquid is displaced from one half of the chamber when filling the other half.

Since ready-made dialysis fluid is supplied, the design of the actual balancing system is simplified inasmuch as it is not necessary to mix water and concentrate(s) by using the balancing chambers of the balancing system.

The dialysis fluid may be prepared by mixing one or more concentrates and water, with the water and concentrates being mixed at one or more mixing points. The mixing points may be located upstream or downstream from the proportioning device. The composition of the mixture of water and concentrates may be monitored by being measured downstream from the respective mixing point. This can be accomplished by a conductivity measurement or by a density measurement.

The water flows during proportioning if a concentrate has not yet been added or the mixture of water and concentrate(s) always has a preselected flow rate regardless of other influences. Thus, only the pauses between switching the chamber halves of the proportioning device depend on the flow of dialysate.

To be sure that a sufficient volume of dialysis fluid can be supplied, the ready-made dialysis fluid is collected. This makes it possible to perform the proportioning in successive cycles.

In a preferred embodiment, to supply a certain reservoir of fresh dialysis fluid, a liquid level indicator and a control unit are provided, so that after the liquid level drops below a predetermined setpoint, the proportioning device switches, causing a certain volume of liquid to be conveyed in cycles at a predetermined flow rate.

The ready-made dialysis fluid is preferably collected in an equalizing chamber that may have an inlet for supplying the ready-made dialysis fluid and an outlet for removing same, the dialysis fluid preferably being conveyed into the balancing system by means of a pump connected to the supply line. Since the balancing system does not convey liquid continuously but only in cycles, a recirculation line, preferably with a pressure relief valve connected to it, branches off from the supply line. If a certain excess pressure builds up in the supply line, the excess dialysis fluid can be recirculated.

A vent opening is preferably provided above the liquid level in the equalizing chamber, so that gas (dissolved or undissolved) entrained with the dialysis fluid is automatically separated. Thus, additional air separators can be omitted in principle.

The concentrate or the individual concentrates are preferably supplied in containers, e.g., canisters or bags to which concentrate lines leading to the individual mixing points are connected. However, it is also possible for the concentrates to be supplied from a central concentrate supply.

Water for preparing the dialysis fluid is preferably degassed and/or heated before entering the balancing chamber. The degassing and heating unit remains free of concentrates except in rinsing operations or in emptying the concentrate bags.

BRIEF DESCRIPTION OF THE DRAWINGS

One embodiment of the present invention is described in greater detail below with reference to the drawings, which show.

DETAILED DESCRIPTION OF THE DRAWINGS

Figure 1:
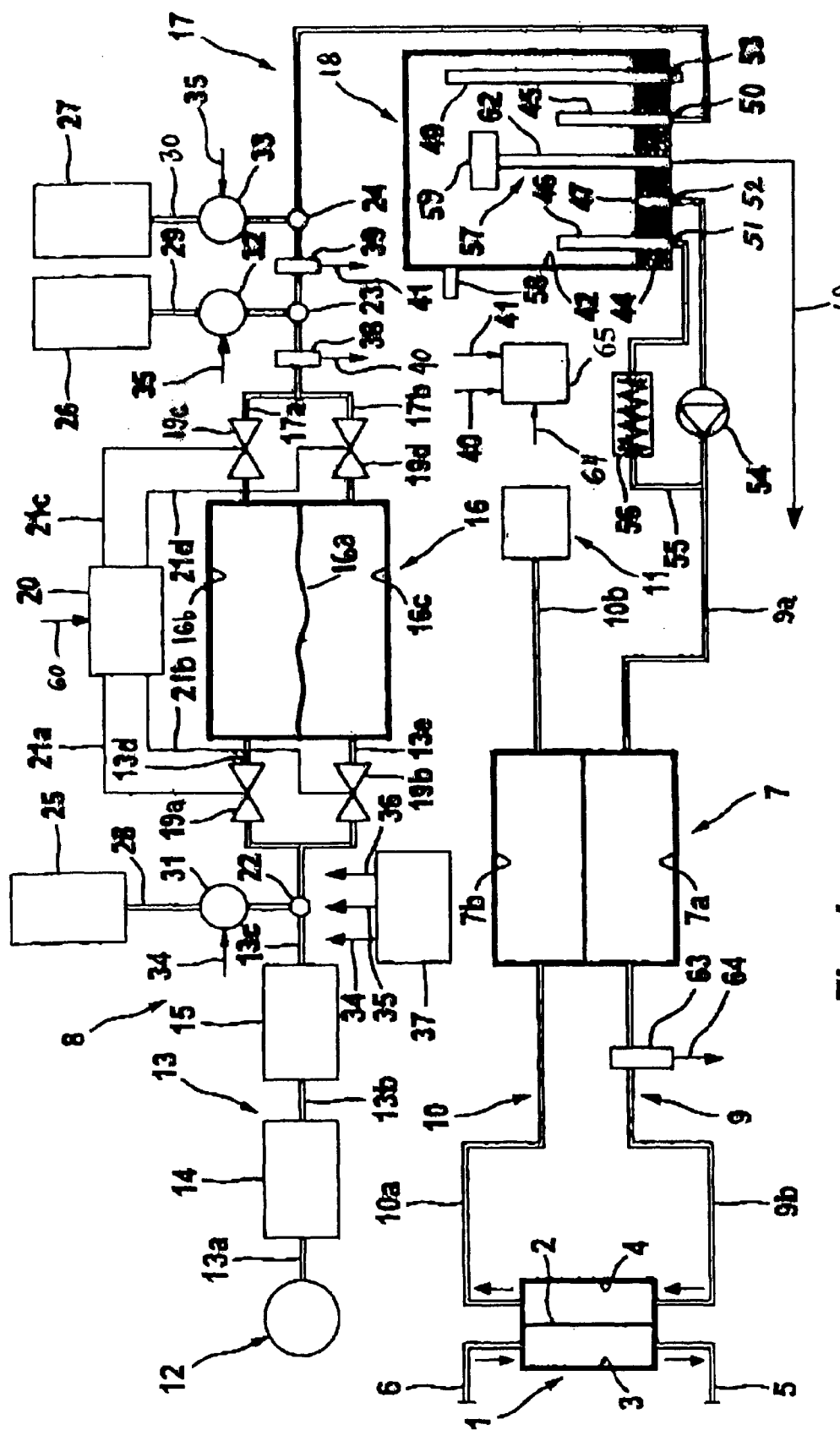
FIG. 1 is a simplified schematic diagram of a preferred embodiment of a dialysis machine having a proportioning device according to this invention.

FIG. 1 shows the essential components of a dialysis machine in a simplified schematic diagram together with the proportioning device. The dialysis machine has a dialyzer 1 which is subdivided by a semipermeable membrane 2 into a chamber 3 for a fluid to be purified and a dialysis fluid chamber 4. The fluid to be purified may be blood, for example. Thus, this chamber is referred to hereinafter as a blood chamber. However, it is understood that chamber 3 may contain a variety of other substances such as fluid coming from a patient's peritoneal cavity. A blood supply line 6 is connected to the inlet of the blood chamber and a blood outlet line 5 is connected to the outlet of the blood chamber. For balancing fresh and spent dialysis fluid, the dialysis machine has a balancing system 7 which has a balancing chamber divided into two balancing chamber halves 7a, 7b. However, the balancing system may also have two balancing chambers connected in parallel.

Fresh dialysis fluid is prepared in a proportioning device 8, to be described in detail below. A first section 9a of a supply line 9 for dialysis fluid leads to an inlet of the first chamber half 7a of balancing chamber 7, while a second section 9b of the supply line leads from an outlet of the first balancing chamber half to an inlet of the dialysis fluid chamber 4. A first line section 10a of a line 10 for spent dialysis fluid leads from an outlet of dialysis fluid chamber 4 and to an inlet of the second balancing chamber half 7b of the balancing chamber. A second section 10b of line 10 leads from an outlet of the second balancing chamber half 7b to an outlet 11. During operation of the dialysis machine, fresh dialysis fluid flows through dialysis fluid chamber 4 of the dialyzer, while blood flows in countercurrent through blood chamber 3 of the dialyzer. For the sake of simplicity, this diagram does not show the blood pump and dialysis fluid pump in the blood and dialysis fluid lines.

Proportioning device 8 for supplying the dialysis fluid is described in detail below. Proportioning device 8 has a source 12 for fresh water. The fresh water may be supplied in a container, e.g., a tank. However, the proportioning device may also be supplied with sufficient fresh water through an external supply system.

A first section 13a of an inlet line 13 leads away from the water source 12 and to a heating unit 14 in which the fresh water is heated to the patient's body temperature. A second section 13b of the inlet line 13 connects the heating unit 14 to a degassing unit 15 for removing gas from the fresh water. A third section 13c of the inlet line 13 leads from the degassing unit 15 to a proportioning unit. The proportioning unit preferably includes a proportioning chamber 16 which is subdivided by a movable partition 16a into two proportioning chamber halves 16b, 16c. The proportioning chamber 16 of the proportioning device 8 has in principle the same design as the balancing chamber of the balancing system 7 of the dialysis machine. Instead of a proportioning chamber, however, two proportioning chambers that work in push-pull operation may also be used. Such an arrangement is described in German Patent Application 197 08 391 A, for example.

The first branch 13d of inlet line 13 is connected to the inlet of the first chamber half 16b, and the second branch 13e of inlet line 13 is connected to the inlet of the second chamber half 16c of proportioning chamber 16. An outlet line 17 connects proportioning chamber 16 to an equalizing chamber 18. Outlet line 17 has a first and second branch 17a, 17b, the first branch 17a leading from the first proportioning chamber half 16b of proportioning chamber 16 and the second branch 17b leading from the second proportioning chamber half 16c. A cutoff element 19a, 19b, 19c, 19d is connected to the branches of inlet and outlet lines 13, 17. The cutoff elements are electromagnetic valves controlled by a control unit 20 over control lines 21a, 21b, 21c, 21d. Control unit 20 controls the cutoff elements so that one of the two chamber halves of proportioning chamber 16 is filled with liquid, so that liquid is discarded from the other chamber half. A fixed flow rate in outlet line 17 is obtained from the filling time of the proportioning chamber, which is determined by the loading flow of fresh water source 12 and the chamber volume. Proportioning chamber 16 in combination with an equalizing chamber 18 thus makes it possible to convey liquid in cycles at a constant flow rate regardless of the operating states of the other components of the dialysis machine. The equalizing chamber will be described in detail below.

To produce the ready-made dialysis fluid, fresh water is mixed with three concentrates at three successive mixing points 22, 23, 24. The first mixing point 22 is located upstream from proportioning chamber 16 in the third section 13c of the inlet line, and the second and third mixing points 23, 24 are located downstream from proportioning chamber 16 in outlet line 17. Metering sections, for example, may be provided at mixing points 22, 23, 24 in inlet and outlet lines 13, 17. The three concentrates are prepared in containers, in particular in bags 25, 26, 27 which are connected to the mixing points by concentrate lines 28, 29, 30. Proportioning pumps 31, 32, 33 are connected to the concentrate lines and are also connected to a second control unit 37 over control lines 34, 35, 36. Proportioning is volumetric as a function of the chamber volume, so that the desired mixing ratio is achieved. A first conductivity sensor 38 is provided in outlet line 17 to measure the conductivity of the dialysis fluid downstream from the first mixing point 22 and upstream from the second mixing point 23, and a second conductivity sensor 39 is provided for measuring the conductivity downstream from the second mixing point 23. A third conductivity sensor 63 for measuring the total conductivity is provided upstream from the dialyzer. Measured values from conductivity sensors 38, 39, 63 are transmitted over data lines 40, 41, 64 to a monitoring unit 65. Control unit 37 sets the pump volumes of proportioning pumps 31, 32, 33 to yield a dialysis fluid having the desired composition. Temperature compensation is preferably performed with the conductivity measurement. Outlet line 17 of the proportioning device leads to equalizing chamber 18.

Figure 2:
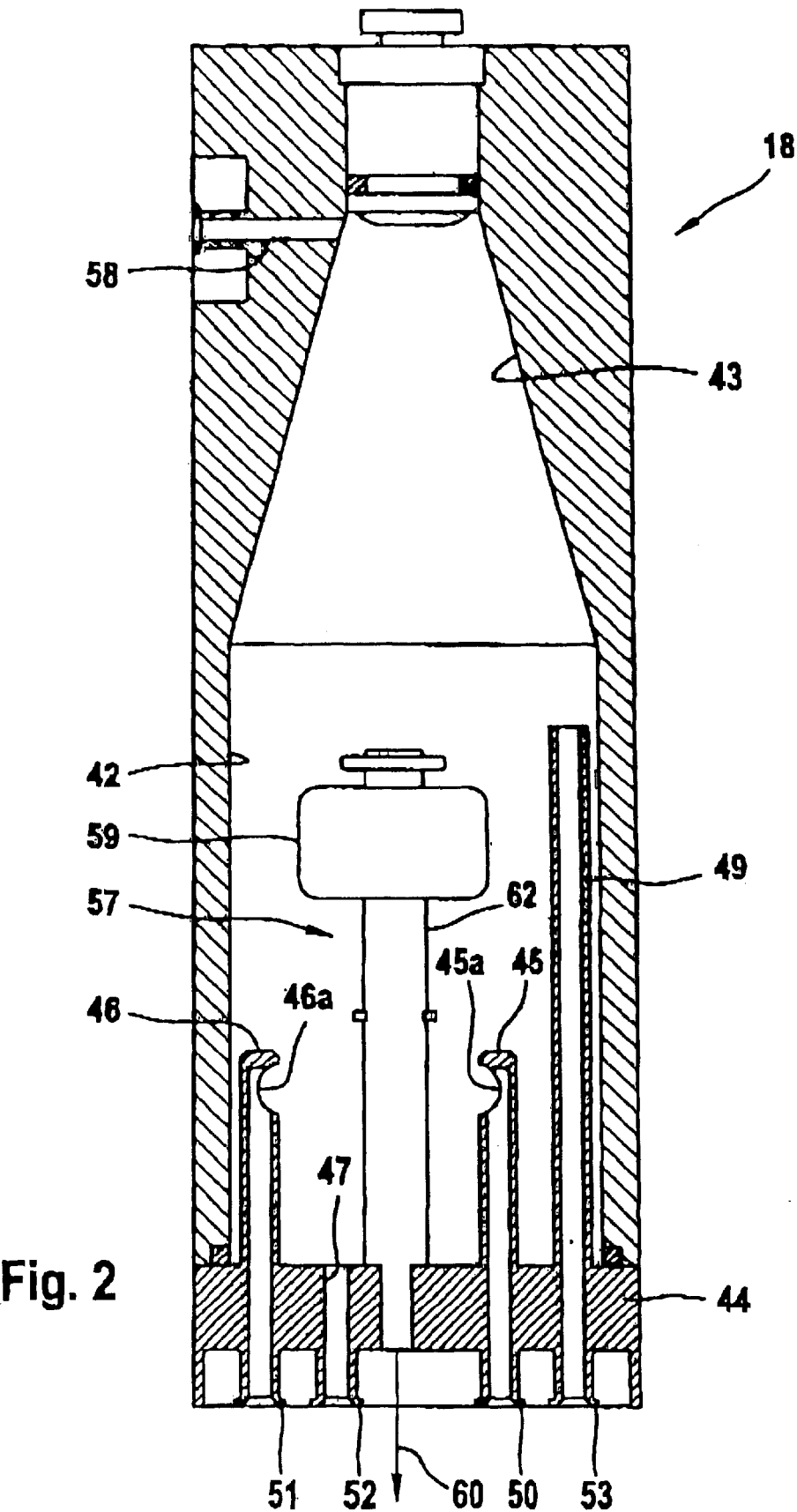
FIG. 2 is a first embodiment of the equalizing chamber of the proportioning device shown in FIG. 1.

FIG. 1 shows only a schematic diagram of equalizing chamber 18. The equalizing chamber may have different designs. FIG. 2—which is to be considered in conjunction with FIG. 1—shows a preferred embodiment of the equalizing chamber, which has an essentially cylindrical bottom space 42 connected to an essentially conical top space 43. However, the chamber described in German Patent Application 199 29 327.9 may also be used as an equalizing chamber.

For the sake of simplicity, FIG. 1 shows only the essential components of the dialysis machine having the proportioning device. Other components may also be provided, e.g., additional safety valves, pressure sensors.

All the connections of equalizing chamber 18, except the rinsing connection, are located on chamber bottom 44. The equalizing chamber has an inlet connection 45 and a recirculation connection 46 extending through the chamber bottom 44 into cylindrical space 42. Inlet connection 45 and recirculation connection 46 each have a liquid outlet 45a, 46a bent perpendicular to the longitudinal axis of the chamber, so that liquid flows into the cylindrical space of the chamber in the horizontal direction. An outlet connection 47 is provided in chamber bottom 44. In addition, a vent tube 49 extends through chamber bottom 44 up to the vicinity of conical space 43 of equalizing chamber 18, which may also function as an overflow tube.

The inlet connection, outlet connection and recirculation connection as well as vent tube 49 have connectors 50, 51, 52, 53 on the chamber bottom. Outlet line 17 is connected to connector 50 of inlet connection 45. Supply line 9 (FIG. 1) is connected to connector 52 of outlet connection 47.

A loading pump 54 is connected to the first section 9a of supply line 9 to withdraw ready-made dialysis fluid from the equalizing chamber. Downstream from loading pump 54, a recirculation line 55 which is connected to connector 51 of recirculation connection 46 branches off from the first section 9a of supply line 9. A pressure relief valve 56 connected to recirculation line 55 releases the flow connection to the equalizing chamber only when a certain excess pressure is exceeded.

A liquid level indicator 57 is provided for monitoring the liquid level in the equalizing chamber. At the center of cylindrical space 42, liquid level indicator 57 has a rod 62 along which a float 59 is guided displaceably in the longitudinal direction of the chamber. If the liquid level in the equalizing chamber drops below a predetermined setpoint, the liquid level indicator delivers a control signal to control unit 20 over data line 60.

A vent pipe is provided for separation of air that may be entrained in the ready-made dialysis fluid. A rinse pipe 58 which opens into equalizing chamber 18 at the upper end of conical space 43 is provided for rinsing the equalizing chamber. A rinse line (not shown) through which rinse liquid flows into the equalizing chamber may be connected to rinse pipe 58. Rinse liquid then flows down along the inside wall of conical space 43 and cylindrical space 42, so that the entire chamber is completely wetted.

The function of the proportioning device is described in detail below. Control unit 20 controls the cutoff elements such that cutoff elements 19a and 19d are opened and cutoff elements 19b and 19c are closed. After being heated in heating unit 14 and degassed in degassing unit 15, fresh water from water source 12 flows through the first branch 13d of inlet line 13 into first chamber half 16b of proportioning chamber 16. During the filling of first chamber half 16b, an individual concentrate provided specifically for that patient is removed from bag 25 by means of proportioning pump 31, whose flow rate is set by control unit 20 and added at the first mixing point 22. The filling time of the first chamber half is preferably 1.2 second, which corresponds to a flow rate of 1500 mL/min in outlet line 17. The metering operation begins with the opening of cutoff elements 19a, 19d and after closing cutoff elements 19b, 19c and it ends after about 0.9–1.0 second, so that enough time remains to convey the total amount of individual concentrate into the first chamber half.

During the filling of the first chamber half 16b, the movable membrane forces the mixture of fresh water and individual concentrate out of the second chamber half from a previous cycle into outlet line 17. At the second mixing point 23, bicarbonate concentrate from bag 26 is added by using proportioning pump 32, and at the third mixing point 24, acid concentrate from bag 27 is added by using proportioning pump 33. The conductivity of the mixture of fresh water and individual concentrate is monitored by the first conductivity sensor 38. The conductivity of the bicarbonate concentrate added is monitored by the second conductivity sensor 39, the addition of bicarbonate being determined by calculating the measured values. The total conductivity of the dialysis fluid is monitored by the third conductivity sensor 63 downstream from equalizing chamber 18 and upstream from dialyzer 1, which is connected to monitoring unit 65 by a data line 64. The addition of bicarbonate concentrate and acid concentrate begins with the opening of cutoff elements 19a, 19d and after closing the cutoff elements 19b, 19c. The metered addition time of bicarbonate and acid is such that the total amount of concentrates is conveyed through outlet line 17 into equalizing chamber 18. The flow rate at which the liquid flows through the outlet line depends only on the loading flow of the fresh water source and the chamber volume. If the flow rate of the dialysis fluid through the dialysis fluid chamber 4 of the dialyzer should change, this has no effect on the flow rate in the outlet line. This has the advantage that the conductivity can be measured with a high accuracy regardless of changes in flow, and the metered addition of the concentrates can be performed accurately.

Instead of individual concentrate dialysis, however, it is also possible to perform acetate dialysis in which acetate is added only at the third mixing point 24 or bicarbonate dialysis in which bicarbonate is added at the second mixing point 23 and acid concentrate is added at the third mixing point 24 but no individual concentrate is added.

Equalizing chamber 18 provides a variable buffer volume between proportioning chamber 16 of the proportioning device and balancing system 7 of the dialysis machine. It equalizes volume tolerances and promotes thorough mixing of the dialysis fluid. It also serves to provide venting.

Equalizing chamber 18 is filled with dialysis fluid in cycles, so that alternately the first and second chamber halves 16b, 16c of proportioning chamber 16 are filled using liquid from the other chamber half. To fill the second chamber half 16c, control unit 20 controls the cutoff elements so that cutoff elements 19b and 19c are opened and cutoff elements 19a and 19d are closed.

The ready-made dialysis fluid is removed from equalizing chamber 18 by loading pump 54 and sent to the balancing chamber of balancing system 7 of the dialysis machine. The loading time of the balancing chamber of the balancing system of the dialysis machine is preferably 1.5 seconds, which corresponds to a flow rate of 1200 mL/min. After the end of the balancing chamber filling time, the loading pressure increases, so that pressure relief valve 56 in recirculation line 55 opens and dialysis fluid is returned to the equalizing chamber.

The cutoff elements of proportioning chamber 16 of proportioning device 8 are controlled as a function of the control signal of liquid level indicator 57 in equalizing chamber 18. If the liquid level in the equalizing chamber drops below the given setpoint, the control unit controls the cutoff elements so that the proportioning chamber 16 is switched. The next proportioning chamber switch can take place, at the earliest, 1.5 seconds after the last switch. This ensures that the loading time of proportioning chamber 16 does not drop below 1.2 seconds. If the liquid level in the equalizing chamber does not increase after proportioning chamber 16 is switched to the extent that the switching point of the liquid level indicator is exceeded, then the proportioning chamber 16 is switched again after a brief dead time during which the control unit 20 closes all the cutoff elements. This takes place until the desired liquid level is reached in equalizing chamber 18. Since the volume of proportioning chamber 16 of proportioning device 8 and the volume of the concentrate added are approximately equal to the volume of balancing chamber 16 of balancing system 7 of the dialysis machine, both of the chambers are usually switched in synchronization. Only in individual cases will proportioning chamber 16 be switched twice in immediate succession. The pause between the two switching operations varies as a function of the set flow rate of the dialysis fluid. For example, at a dialysis fluid flow rate of 1000 mL/min, the balancing chamber cycle is 1.8 seconds and at 100 mL/min it is 18 seconds. However, the filling and emptying of proportioning chamber 16 still take only 1.2 seconds each. In the event of a disturbance, excess dialysis fluid can flow out through vent pipe 49.

Figure 3:
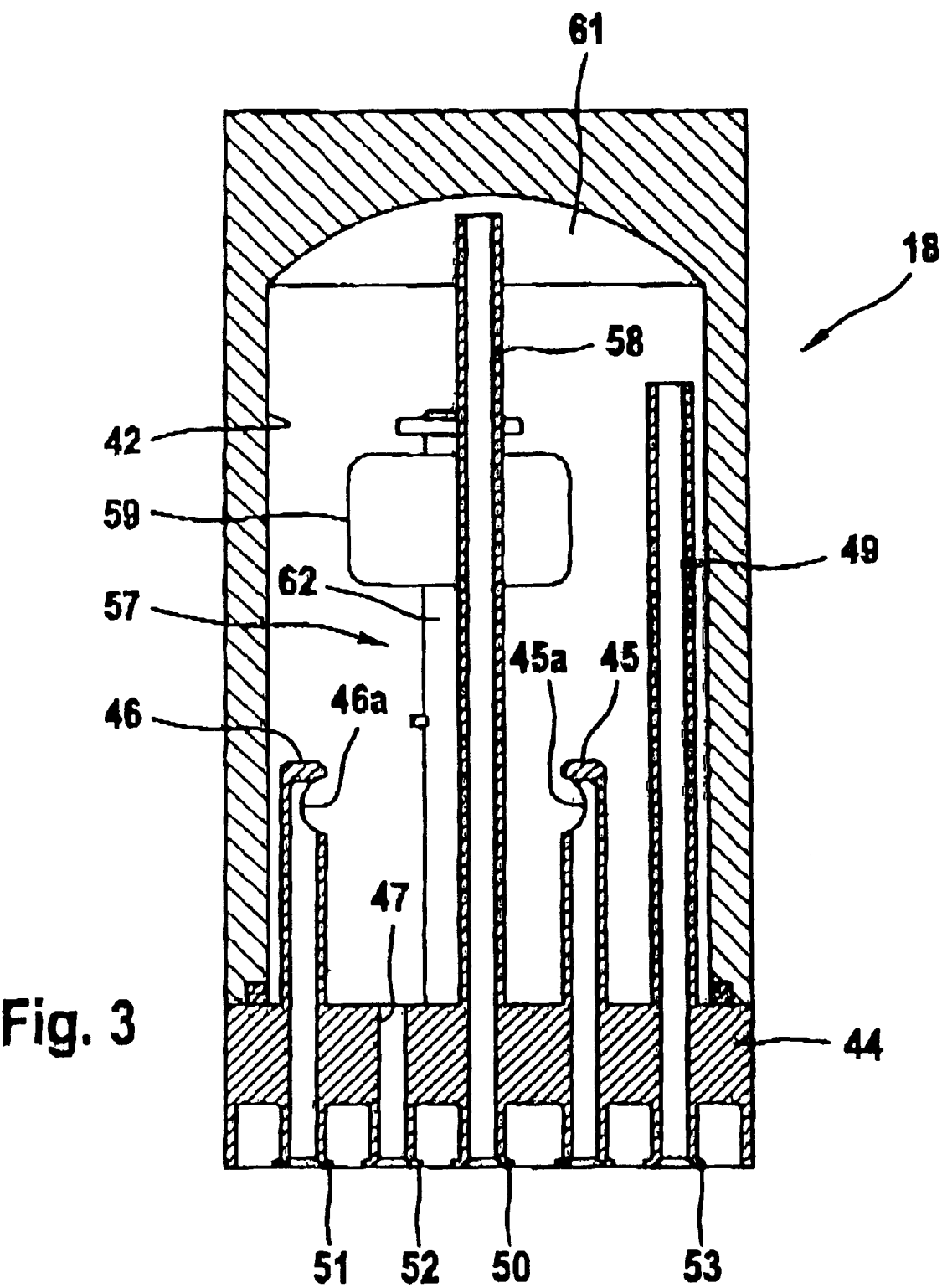
FIG. 3 is a second embodiment of the equalizing chamber of the proportioning device shown in FIG. 1.

FIG. 3 shows a second embodiment of the equalizing chamber. The parts of the equalizing chamber in FIG. 3 which correspond to those of the chamber in FIG. 2 are labeled with the same reference numbers. The chamber of FIG. 3 differs from the chamber in FIG. 2 in the shape of the housing and also in the arrangement of the rinse pipe. The equalizing chamber does not have a conical container cover 61, but instead it curves outward (dome). Rinse pipe 58 does not open into the chamber at the side, but instead extends upward through chamber bottom 44 to just below the wall of the dome. The equalizing chamber is cleaned by spraying rinsing solution under pressure onto the dome wall from beneath. The rinsing solution then runs down uniformly on all sides of the wall, so that the entire inside surface of the chamber is cleaned. Otherwise, the equalizing chamber of FIG. 3 has the same function as the chamber in FIG. 2.

While the foregoing description and drawings represent the preferred embodiments of the present invention, it will be apparent to whose skilled in the art that various changes and modifications may be made therein without departing from the true spirit and scope of the present invention.

What is claimed is:

1. A dialysis machine comprising:

a dialyzer subdivided by a semipermeable membrane into a chamber for a liquid to be purified and a dialysis fluid chamber;

a dialysis fluid inlet line leading to an inlet of the dialysis fluid chamber;

a dialysis fluid outlet line leading away from an outlet of the dialysis fluid chamber;

a balancing system connected to the dialysis fluid inlet and outlet lines for balancing fresh and spent dialysis fluid; and a proportioning device for supplying fresh dialysis fluid, the proportioning device comprising:

a water source;

at least one proportioning unit having a first chamber half and second chamber half configured to operate so that liquid is displaced from one chamber half when the other chamber half is filled with liquid;

a proportioning unit inlet line leading from the water source, the proportioning unit inlet line connected to an inlet of the first chamber half and an inlet of the second chamber half, and a proportioning unit outlet line connected to an outlet of the first chamber half and an outlet of the second chamber half, so that the chamber halves can be alternately filled and emptied;

at least one mixing point provided in at least one of the proportioning unit inlet line and the proportioning unit outlet line;

at least one dialysis fluid concentrate source for supplying a fluid concentrate to the at least one mixing point for forming a fresh dialysis fluid; and an equalizing chamber for the fresh dialysis fluid, the equalizing chamber connected to the proportioning unit outlet line, wherein the equalizing chamber provides a variable buffer volume between the proportioning unit and the balancing system such that the flow rate of a dialysis fluid through the dialysis fluid chamber has no effect on the flow rate of the fresh dialysis fluid in the proportioning unit outlet line.

2. The dialysis machine according to claim 1, wherein one mixing point is provided in the proportioning unit inlet line, and at least one mixing point is provided in the proportioning unit outlet line.

3. The dialysis machine according to claim 1, wherein the proportioning unit inlet line has a first inlet branch in fluid communication with the inlet of the first chamber half and a second inlet branch in fluid communication with the inlet of the second chamber half, and wherein the proportioning unit outlet line has a first outlet branch in fluid communication with the outlet of the first chamber half and a second outlet branch in fluid communication with the outlet of the second chamber half, the machine further comprising a first inlet cutoff element provided in the first inlet branch, a second inlet cutoff element provided in the second inlet branch, a first outlet cutoff element provided in the first outlet branch, and a second outlet cutoff element provided in the second outlet branch.

4. The dialysis machine according to claim 3, wherein the equalizing chamber further comprises:

a liquid level indicator; and a control unit to control the first inlet cutoff element, the second inlet cutoff element, the first outlet cutoff element, and the second outlet cutoff element after a liquid level drops below a predetermined setpoint.

5. The dialysis machine according to claim 1, wherein the equalizing chamber further comprises:

an outlet connected to a supply line;

a first inlet connected to the proportioning unit outlet line; and a second inlet connected to a recirculation line branching off from the supply line.

6. The dialysis machine according to claim 5, further comprising:

a pressure relief valve connected to the recirculation line.

7. The dialysis machine according to claim 5, further comprising:

a vent pipe in the equalizing chamber.

8. The dialysis machine according to claim 1, wherein the at least one dialysis fluid concentrate source comprises a first concentrate container for holding a first concentrate, the first concentrate container in fluid connection with a first concentrate line in fluid communication with a first mixing point in the proportioning unit inlet line upstream from the proportioning unit.

9. The dialysis machine according to claim 8, wherein the at least one dialysis fluid concentrate source further comprises a second container for holding a second concentrate, the second concentrate container in fluid connection with a second concentrate line in fluid communication with a second mixing point in the proportioning unit outlet line downstream from the proportioning unit.

10. The dialysis machine according to claim 9, wherein the at least one dialysis fluid concentrate source further comprises a third container for holding a third concentrate, the third concentrate container in fluid connection with a third concentrate line in fluid communication with a third mixing point in the proportioning unit outlet line downstream from the second mixing point.

11. The dialysis machine according to claim 10, wherein proportioning pumps are connected to at least one of the first concentrate line, second concentrate line, and third concentrate line for adjusting the volume of the dialysis fluid concentrate.

12. The dialysis machine according to claim 1, wherein at least one conductivity sensor is provided for measuring the conductivity of a mixture of the water and the dialysis fluid concentrate downstream from a mixing point.

13. The dialysis machine according to claim 1, further comprising:

at least one of a degassing and a heating unit connected to the proportioning unit inlet line.

14. A method of operating a dialysis machine, comprising the steps of:

sending fresh dialysis fluid to a dialysis fluid chamber of a dialyzer, the chamber divided by a semipermeable membrane into the dialysis fluid chamber and a chamber for the liquid to be purified;

removing dialysis fluid from the dialysis fluid chamber; and balancing spent and fresh dialysis fluid in a balancing system whereby the fresh dialysis fluid is prepared by:

filling alternately a first and a second chamber half of at least one proportioning unit with at least one of water and a mixture of water and at least one dialysis fluid concentrate;

discarding a liquid from the other chamber half;

adding at least one dialysis fluid concentrate to the liquid discarded from the other chamber half and a liquid supplied to the chamber to prepare the fresh dialysis fluid;

collecting the fresh dialysis fluid in an equalizing chamber before the fresh dialysis fluid is sent to the dialysis fluid chamber, wherein the equalizing chamber provides a variable buffer volume between the at least one proportioning unit and the balancing system such that the flow rate of the dialysis fluid through the dialysis fluid chamber has no effect on the flow rate of the fresh dialysis fluid into the equalizing chamber.

15. The method according to claim 14, wherein a liquid level is monitored within the equalizing chamber, and further comprising the step of:

switching the at least one proportioning unit until the liquid level is again above a predetermined setpoint after the liquid level drops below the predetermined setpoint.

16. The method according to claim 15, further comprising the steps of:

removing the dialysis fluid from the equalizing chamber; and returning a portion of the liquid to the equalizing chamber.

17. The method according to claim 15, further comprising the step of:

degassing the dialysis fluid in the equalizing chamber.

18. The method according to claim 14, further comprising the step of:

degassing at least one of the water and the mixture of the water and the dialysis fluid before at least one of the water and the mixture of the water and the dialysis fluid enter the at least one proportioning unit.

19. The method according to claim 14, further comprising the step of:

heating the at least one of the water and the mixture of the water and the dialysis fluid before at least one of the water and the mixture of the water and the dialysis fluid enter the at least one proportioning unit.

20. The method according to claim 14, further comprising the step of:

measuring the composition of the mixture of water and the at least one dialysis fluid concentrate by determining the conductivity of the mixture downstream from a mixing point.

* * * * *

(12) EX PARTE REEXAMINATION CERTIFICATE (6988th)
United States Patent
Balschat et al.

(10) Number: US 6,595,944 C1
(45) Certificate Issued: Aug. 11, 2009

(54) DIALYSIS MACHINE AND METHOD OF OPERATING A DIALYSIS MACHINE

(75) Inventors: Klaus Balschat, Schwebheim (DE); Michael Koch, Schweinfurt (DE); Elmar Wolter, Estenfeld (DE)

(73) Assignee: Fresenius Medical Care Deutschland GmbH, Bad Homburg (DE)

Reexamination Request:
No. 90/008,867, Oct. 4, 2007

Reexamination Certificate for:
Patent No.: 6,595,944
Issued: Jul. 22, 2003
Appl. No.: 09/882,337
Filed: Jun. 15, 2001

(51) Int. Cl.
*A61M 37/00* (2006.01)
*A61M 1/16* (2006.01)
*B01F 3/08* (2006.01)
*B01F 15/04* (2006.01)

(52) U.S. Cl. .................. 604/6.09; 604/6.11; 604/5.04; 210/645; 210/646

(58) Field of Classification Search .............. 604/6.09, 604/6.11, 29–31, 4.01, 5.01, 5.04

See application file for complete search history.

(56) References Cited

U.S. PATENT DOCUMENTS

| 3,605,783 | A | * | 9/1971 | Pecker et al. | ............... 137/93 |
| 3,672,389 | A | * | 6/1972 | McConnell et al. | ........... 137/99 |
| 4,136,708 | A | | 1/1979 | Cosentino | |
| 4,388,184 | A | | 6/1983 | Brous | |
| 4,770,769 | A | | 9/1988 | Schael | |
| 5,486,286 | A | | 1/1996 | Peterson | |
| 6,042,784 | A | | 3/2000 | Wamsiedler | |

FOREIGN PATENT DOCUMENTS

| DE | 3234119 | 11/1983 |
| DE | 19702211 | 7/1998 |
| GB | 2069855 | 9/1981 |

* cited by examiner

*Primary Examiner*—Catherine S. Williams

(57) ABSTRACT

A machine and method for preparing dialysis fluid for a dialysis machine. Fresh water is mixed with one or more dialysis fluid concentrates. The mixture of water and concentrates is conveyed into a equalizing chamber by a proportioning unit at a predetermined flow rate independent of the dialysate flow rate. Metered addition of the concentrates is performed volumetrically and is monitored on the basis of the conductivity of the dialysis fluid, which is measured by conductivity sensors. Because the mixture of water and concentrates is always conveyed at the same flow rate, the composition of the dialysis fluid can be determined with a high accuracy and the proportioning can be performed accurately.

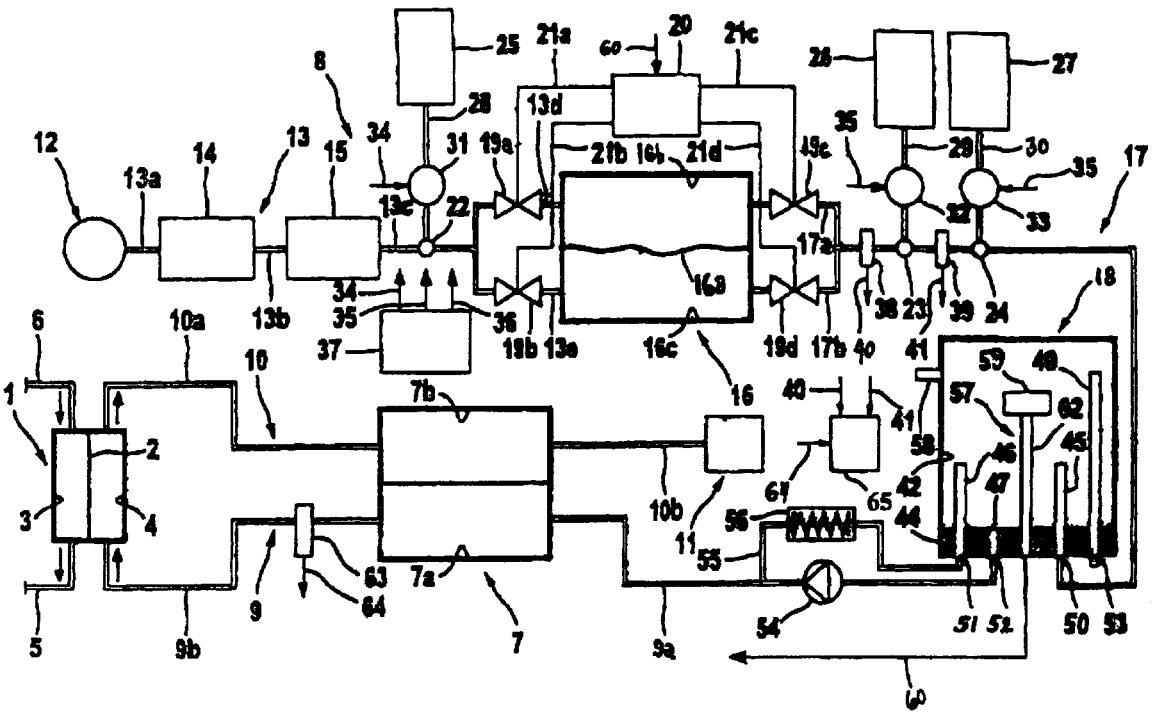

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–20 is confirmed.

New claims 21–49 are added and determined to be patentable.

21. *The dialysis machine of claim 1, wherein the inlet of the first chamber half and the outlet of the first chamber half are separate.*

22. *The dialysis machine of claim 1, wherein the inlet of the second chamber half and the outlet of the second chamber half are separate.*

23. *The dialysis machine of claim 1, further comprising a first inlet cutoff element to either allow flow into the first chamber half or interrupt flow into the first chamber half.*

24. *The dialysis machine of claim 1, further comprising a first outlet cutoff element to either allow flow out the first chamber half or interrupt flow out of the first chamber half.*

25. *The dialysis machine of claim 1, further comprising a second inlet cutoff element to either allow flow into the second chamber half or interrupt flow into the second chamber half.*

26. *The dialysis machine of claim 1, further comprising a second outlet cutoff element to either allow flow out of the second chamber half or interrupt flow out of the second chamber half.*

27. *The dialysis machine of claim 1, wherein an outlet from the equalizing chamber is connected to an inlet of the balancing system.*

28. *The dialysis machine of claim 1, wherein an inlet from the equalizing chamber is connected to the proportioning unit outlet line.*

29. *The dialysis machine of claim 8, further comprising a conductivity sensor located downstream of the first mixing point.*

30. *The dialysis machine of claim 9, further comprising a conductivity sensor located downstream of the second mixing point.*

31. *The dialysis machine of claim 10, further comprising a conductivity sensor located downstream of the third mixing point.*

32. *The dialysis machine of claim 9, further comprising a first conductivity sensor located downstream of the first mixing point and a second conductivity sensor located downstream of the second mixing point.*

33. *The dialysis machine of claim 10, further comprising a first conductivity sensor located downstream of the first mixing point, a second conductivity sensor located downstream of the second mixing point, and a third conductivity sensor located downstream of the third mixing point.*

34. *The method of operating a dialysis machine of claim 14, wherein the first and second chamber half of the at least one proportioning unit are alternately filled with a mixture of water and at least one dialysis fluid concentrate.*

35. *The method of operating a dialysis machine of claim 14, wherein the first chamber half is filled through a first inlet and the second chamber half is filled through a second inlet.*

36. *The method of operating a dialysis machine of claim 14, wherein the liquid is discarded from first chamber half through a first outlet and the liquid is discarded from the second chamber half through a second outlet.*

37. *The method of operating a dialysis machine of claim 14, wherein the first chamber half further comprises a first inlet and a first outlet and the second chamber further comprises a second inlet and a second outlet.*

38. *The method of operating a dialysis machine of claim 37, wherein the first inlet further comprises a first inlet cutoff element and the first outlet further comprises a first outlet cutoff element.*

39. *The method of operating a dialysis machine of claim 38, wherein the second inlet further comprises a second inlet cutoff element and the second outlet further comprises a second outlet cutoff element.*

40. *The method of operating a dialysis machine of claim 39, further comprising the step of alternately opening the first inlet cutoff element together with the second outlet cutoff element, and opening the second inlet cutoff element together with the first outlet cutoff element to alternately fill the first chamber half and the second chamber half.*

41. *The method of operating a dialysis machine of claim 14, further comprising the steps of: monitoring a liquid level in the equalizing chamber; and when the liquid level drops below a predetermined setpoint, switching which chamber half is being filled and which chamber half is being emptied.*

42. *The method of operating a dialysis machine of claim 14, further comprising the steps of: monitoring a liquid level in the equalizing chamber; and when the liquid level drops below a predetermined setpoint, switching which cutoff elements are opened and which cutoff elements are closed.*

43. *A dialysis machine comprising:*

*a dialyzer subdivided by a semipermeable membrane into a chamber for a liquid to be purified and a dialysis fluid chamber;*

*a dialysis fluid inlet line leading to an inlet of the dialysis fluid chamber;*

*a dialysis fluid outlet line leading away from an outlet of the dialysis fluid chamber;*

*a balancing system connected to the dialysis fluid inlet and outlet lines for balancing fresh and spent dialysis fluid; and*

*a proportioning device for supplying fresh dialysis fluid, the proportioning device comprising:*

*a water source;*

*at least one proportioning unit having a first chamber half and second chamber half configured to operate so that liquid is displaced from one chamber half when the other chamber half is filled with liquid, wherein the first chamber half and the second chamber half are separated by a flexible membrane;*

*a proportioning unit inlet line leading from the water source, the proportioning unit inlet line connected to an inlet of the first chamber half and an inlet of the second chamber half, and a proportioning unit outlet line connected to an outlet of the first chamber half and an outlet of the second chamber half, so that the chamber halves can be alternately filled and emptied;*

*at least one mixing point provided in at least one of the proportioning unit inlet line and the proportioning unit outlet line;* at least one dialysis fluid concentrate source for supplying a fluid concentrate to the at least one mixing point for forming a fresh dialysis fluid; and an equalizing chamber for the fresh dialysis fluid, the equalizing chamber connected to the proportioning unit outlet line, wherein the equalizing chamber provides a variable buffer volume between the proportioning unit and the balancing system such that the flow rate of a dialysis fluid through the dialysis fluid chamber has no effect on the flow rate of the fresh dialysis fluid in the proportioning unit outlet line.

44. The dialysis machine of claim 43, wherein the inlet of the first chamber half and the outlet of the first chamber half are separate.

45. The dialysis machine of claim 43, wherein the inlet of the second chamber half and the outlet of the second chamber half are separate.

46. The dialysis machine of claim 43, further comprising a first inlet cutoff element to either allow flow into the first chamber half or interrupt flow into the first chamber half.

47. The dialysis machine of claim 43, further comprising a first outlet cutoff element to either allow flow out of the first chamber half or interrupt flow out of the first chamber half.

48. The dialysis machine of claim 43, further comprising a second inlet cutoff element to either allow flow into the second chamber half or interrupt flow into the second chamber half.

49. The dialysis machine of claim 43, further comprising a second outlet cutoff element to either allow flow out of the second chamber half or interrupt flow out of the second chamber half.

* * * * *